United States Patent
Allen et al.

(10) Patent No.: US 10,147,047 B2
(45) Date of Patent: Dec. 4, 2018

(54) AUGMENTING ANSWER KEYS WITH KEY CHARACTERISTICS FOR TRAINING QUESTION AND ANSWER SYSTEMS

(71) Applicant: International Business Machines Corporation, Armonk, NY (US)

(72) Inventors: Corville O. Allen, Morrisville, NC (US); Christine A. Grev, Rochester, MN (US); Richard J. Stevens, Monkton, VT (US)

(73) Assignee: International Business Machines Corporation, Armonk, NY (US)

( * ) Notice: Subject to any disclaimer, the term of this patent is extended or adjusted under 35 U.S.C. 154(b) by 842 days.

(21) Appl. No.: 14/591,413

(22) Filed: Jan. 7, 2015

(65) Prior Publication Data
US 2016/0196504 A1     Jul. 7, 2016

(51) Int. Cl.
| | |
|---|---|
| *G06N 99/00* | (2010.01) |
| *G06N 5/04* | (2006.01) |
| *G16H 10/20* | (2018.01) |
| *G16H 50/20* | (2018.01) |

(52) U.S. Cl.
CPC ............. *G06N 99/005* (2013.01); *G06N 5/04* (2013.01); *G16H 10/20* (2018.01); *G16H 50/20* (2018.01)

(58) Field of Classification Search
CPC ........... G06N 99/005; G06N 5/02; G06N 5/04
USPC .......................................................... 706/11
See application file for complete search history.

(56) References Cited

U.S. PATENT DOCUMENTS

| | | | |
|---|---|---|---|
| 7,603,330 B2 | 10/2009 | Gupta et al. | |
| 8,340,955 B2 | 12/2012 | Brown et al. | |
| 8,473,499 B2 | 6/2013 | Song et al. | |
| 8,543,565 B2 | 9/2013 | Feng | |
| 8,738,617 B2 | 5/2014 | Brown et al. | |
| 8,805,756 B2 | 8/2014 | Boss et al. | |
| 8,819,007 B2 | 8/2014 | Brown et al. | |
| 2009/0287678 A1* | 11/2009 | Brown .............. | G06F 17/30654 |
| 2010/0063797 A1 | 3/2010 | Cong et al. | |
| 2011/0066587 A1 | 3/2011 | Ferrucci et al. | |

(Continued)

OTHER PUBLICATIONS

High, Rob, "The Era of Cognitive Systems: An Inside Look at IBM Watson and How it Works", IBM Corporation, Redbooks, Dec. 12, 2012, 16 pages.

(Continued)

*Primary Examiner* — Alan Chen
(74) *Attorney, Agent, or Firm* — Stephen J. Walder, Jr.; Diana R. Gerhardt

(57) ABSTRACT

Mechanisms are provided for implementing training logic for training a Question and Answer (QA) system. A training question, associated with an answer key, is received and processed by the QA system to generate a final answer to the training question and supporting evidence for the final answer based on a corpus of information. The supporting evidence is analyzed to identify one or more evidence attributes and a plurality of correct answer entries in the answer key are searched to identify a matching correct answer entry that matches the final answer. The matching correct answer entry in the answer key is augmented to include the one or more evidence attributes in an augmented answer key and the QA system is trained based on the augmented answer key.

20 Claims, 6 Drawing Sheets

(56) References Cited

U.S. PATENT DOCUMENTS

| | | | |
|---|---|---|---|
| 2011/0125734 A1* | 5/2011 | Duboue | G09B 7/00 707/723 |
| 2012/0016206 A1* | 1/2012 | Ramarajan | G06F 19/345 600/300 |
| 2012/0078837 A1* | 3/2012 | Bagchi | A61B 5/00 706/52 |
| 2013/0007055 A1* | 1/2013 | Brown | G06F 17/30654 707/769 |
| 2013/0018652 A1 | 1/2013 | Ferrucci et al. | |
| 2013/0066886 A1 | 3/2013 | Bagchi et al. | |
| 2014/0006012 A1 | 1/2014 | Zhou et al. | |
| 2014/0172757 A1 | 6/2014 | Liu | |
| 2014/0172883 A1 | 6/2014 | Clark et al. | |
| 2014/0272884 A1 | 9/2014 | Allen et al. | |
| 2014/0280087 A1 | 9/2014 | Isensee et al. | |
| 2014/0297571 A1 | 10/2014 | Beamon et al. | |
| 2014/0298199 A1 | 10/2014 | Johnson, Jr. et al. | |
| 2015/0044659 A1* | 2/2015 | Basu | G09B 7/00 434/350 |

OTHER PUBLICATIONS

McCord, M.C. et al., "Deep parsing in Watson", IBM J. Res. & Dev. vol. 56 No. 3/4 Paper 3, May/Jul. 2012, pp. 3:1-3:15.

Yuan, Michael J., "Watson and healthcare, How natural language processing and semantic search could revolutionize clinical decision support", IBM developerWorks, IBM Corporation, Apr. 12, 2011, 14 pages.

\* cited by examiner

AUGMENTING ANSWER KEYS WITH KEY CHARACTERISTICS FOR TRAINING QUESTION AND ANSWER SYSTEMS

BACKGROUND

The present application relates generally to an improved data processing apparatus and method and more specifically to mechanisms for augmenting answer keys with key characteristics for training question and answer (QA) systems.

With the increased usage of computing networks, such as the Internet, humans are currently inundated and overwhelmed with the amount of information available to them from various structured and unstructured sources. However, information gaps abound as users try to piece together what they can find that they believe to be relevant during searches for information on various subjects. To assist with such searches, recent research has been directed to generating Question and Answer (QA) systems which may take an input question, analyze it, and return results indicative of the most probable answer to the input question. QA systems provide automated mechanisms for searching through large sets of sources of content, e.g., electronic documents, and analyze them with regard to an input question to determine an answer to the question and a confidence measure as to how accurate an answer is for answering the input question.

Examples, of QA systems are Siri® from Apple®, Cortana® from Microsoft®, and the IBM Watson™ system available from International Business Machines (IBM®) Corporation of Armonk, N.Y. The IBM Watson™ system is an application of advanced natural language processing, information retrieval, knowledge representation and reasoning, and machine learning technologies to the field of open domain question answering. The IBM Watson™ system is built on IBM's DeepQA™ technology used for hypothesis generation, massive evidence gathering, analysis, and scoring. DeepQA™ takes an input question, analyzes it, decomposes the question into constituent parts, generates one or more hypothesis based on the decomposed question and results of a primary search of answer sources, performs hypothesis and evidence scoring based on a retrieval of evidence from evidence sources, performs synthesis of the one or more hypothesis, and based on trained models, performs a final merging and ranking to output an answer to the input question along with a confidence measure.

SUMMARY

In one illustrative embodiment, a method in a data processing system comprising a processor and a memory and implementing training logic for training a Question and Answer (QA) system of the data processing system. The method comprises receiving, by the QA system, a training question associated with an answer key and processing, by the QA system, the training question to generate a final answer to the training question and supporting evidence for the final answer based on a corpus of information. The method further comprises analyzing, by the training logic, the supporting evidence to identify one or more evidence attributes and searching, by the training logic, a plurality of correct answer entries in the answer key to identify a matching correct answer entry that matches the final answer. In addition, the method comprises augmenting the matching correct answer entry in the answer key to include the one or more evidence attributes in an augmented answer key and training, by the training logic, the QA system based on the augmented answer key.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
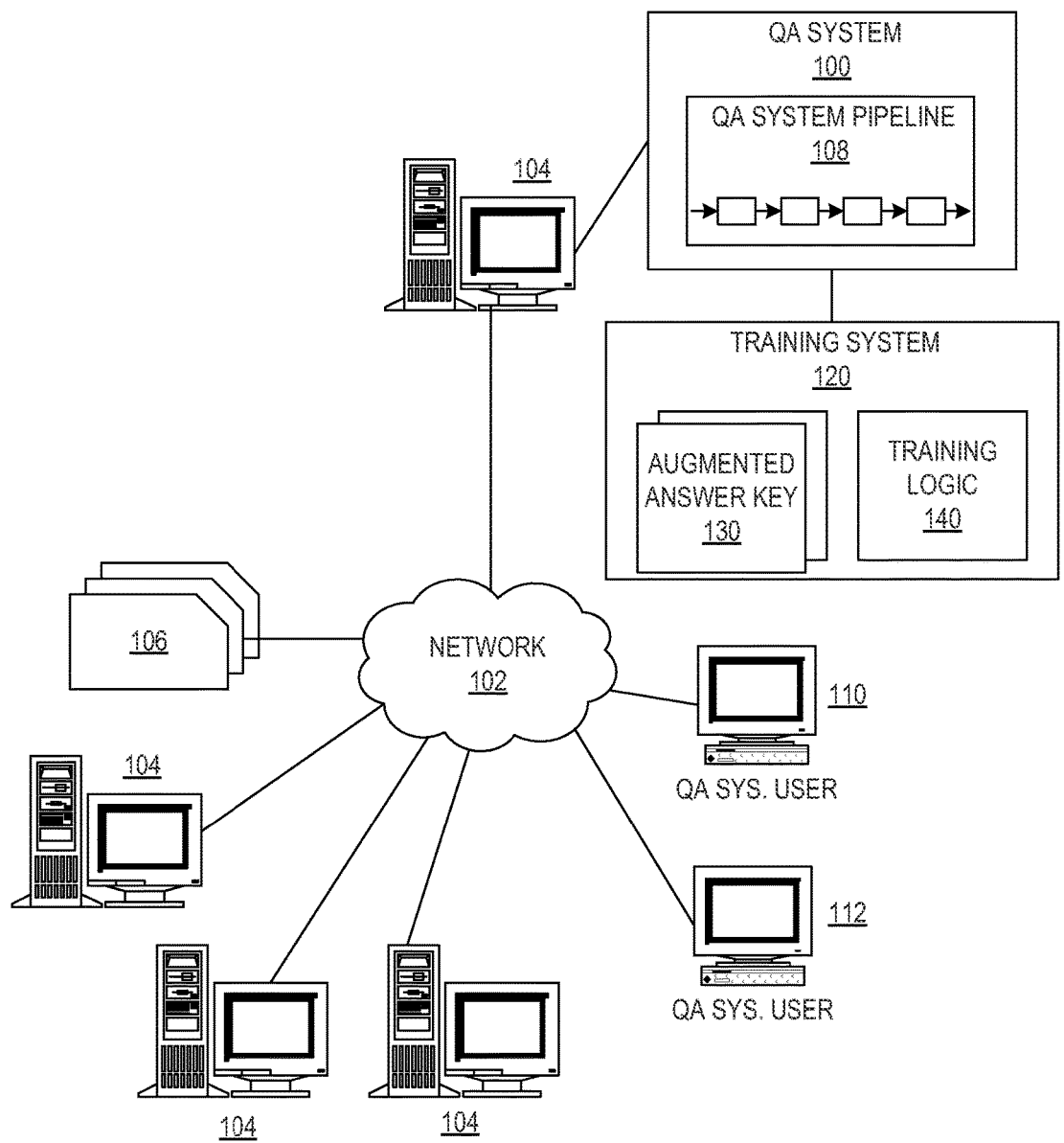
FIG. 1 depicts a schematic diagram of one illustrative embodiment of a question/answer creation (QA) system in a computer network.

The illustrative embodiments provide mechanisms for augmenting an answer key with key characteristics for use in training a question and answer (QA) system, such as the IBM Watson™ QA system available from International Business Machines (IBM) Corporation of Armonk, N.Y. That is, the illustrative embodiments provide mechanisms for improving answer keys (also referred to as ground truth or golden cases) which are used to train the QA system by comparing generated answers to known correct answers for training questions, determining any discrepancies, and modifying a trained statistical model used to modify weights applied to results of annotators so as to increase the likelihood that the QA system will return correct results. A training question is an input of content that explicitly includes a question, or implicitly relates to a question, and may include a single sentence or multiple sentences with additional context data. The additional context data can be any type of supporting data, e.g., medical records, metadata related to the question text, or relevant information that allows for better understanding of the question.

With the mechanisms of the illustrative embodiments, the answer key is augmented to include in the answer key information directly, information about the key characteristics that can be used to decide between multiple correct answers based on the particular conditions or circumstances of the supporting evidence found from the corpus or corpora upon which the QA system operates. That is, known training of QA systems involves the use of answer keys to identify correct versus incorrect answers. An answer in an answer key is correct for all circumstances and all conditions of the evidence of the corpus. That is, a single correct answer is provided in the answer key for a corresponding training question. If a final answer is generated by the QA system that matches an answer for the training question in the answer key, then it is determined to be the correct answer and the QA system is determined to be operating properly. However, there are instances where multiple correct answers are possible for the same training question, with each answer being correct under difference circumstances. In other words, in some domains, "correctness" is a relative term, rather than an absolute one as is generally implemented in known QA system training The illustrative embodiments provide a mechanism to define a spectrum of acceptable answers and the circumstances or conditions in which they apply. This spectrum is defined in the answer key used to train the QA system by supplementing entries in the QA system with key attributes used to differentiate circumstances and conditions in which one answer should be preferred over another, or considered "more correct" than another answer. The particular answer of an entry is considered to be the correct answer when corresponding attributes of the supporting evidence for a final answer are found to align with corresponding attributes of the entry in the answer key.

For example, if a question or request is received by the QA system and requests a recommendation as to a treatment for a particular patient A's particular cancer, multiple possible treatments may be "correct," e.g., a high bone marrow blast, Ara-c (high intensity), etc. However, depending on other factors of patient A's condition, one answer may be more correct than the other. For example, if patient A has an age of 80, Ara-c (high intensity) may be a less correct answer than the high bone marrow blast option. If patient A has an age of less than 40, then Ara-c (high intensity) may be the more correct answer for providing a recommended treatment. The answer key may be augmented to include such conditions of age in association with these answers so as to train the QA system to look at and evaluate these conditions when generating a candidate answer for future requests/questions.

It should be noted that an answer key entry augmented with answer correlation attributes can also serve as a template for multiple training cases, i.e. training question and corresponding correct answer. That is, the spectrum of correct answers for all training cases which align on the specified set of correlation attributes may be designated and used to train the QA system. These separate sets of correlation attributes may in fact be established as separate answer keys where each answer key corresponds to a particular set of correlation attributes and the correct answer key is selected based on the determined attributes from the supporting evidence of the final answer generated by the QA system.

In addition, it should be appreciated that in some domains, the best answer for a particular request or question may not always be the optimal answer for a particular individual. That is, based on the particular individual's own preferences, the best answer may not be the optimal answer and instead another answer may be more correct for the particular individual based on their preferences. As one example, consider a situation in which the therapy option for treating a malady, such as cancer, that has the best odds of being cured may cause hair loss and nausea. However, this therapy option may not be the optimal choice for a particular patient if they 1) have a major public event and do not want to deal with hair loss or 2) they have a very low tolerance for feeling nauseous. To accommodate such personal preferences, the answer key may be augmented to include key correlation attributes that reflect the particular personal preferences of the subject of the request or question, e.g., the patient in the above examples, to differentiate between circumstances or conditions where one answer may be more correct than another for the particular subject of the request/question. These personal preferences may be used to train the QA system to reflect optimal recommendations when personal preferences are taken into account. Such personal preferences of a particular user may be supplied as input to the QA system with the request/question or otherwise identified through analysis of the corpus, e.g., patient medical history documents, or other such data structure. Candidate answers may be scored appropriate based on whether personal preferences are met by the candidate answer or not.

Thus, the mechanisms of the illustrative embodiments provide the ability to rank correctness of answers based on alignment of the answers with a specified set of key attributes identifying conditions under which one answer is more correct than another. Moreover, the mechanisms of the illustrative embodiments provide the ability to define an answer key template that can be used for multiple training cases. In addition, the illustrative embodiments provide mechanisms that can factor in personal preferences to answer evaluation that may not generate answers that are optimal, but factor in request/question subject bias for other factors associated with the answer.

Before beginning the discussion of the various aspects of the illustrative embodiments in greater detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
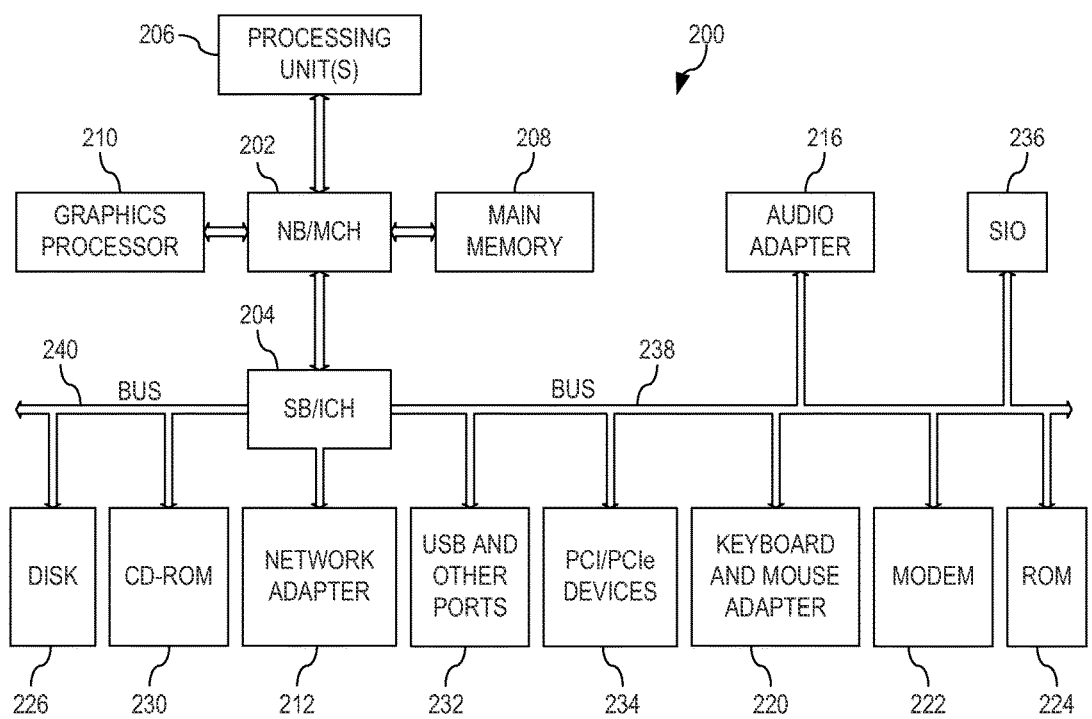
FIG. 2 is a block diagram of an example data processing system in which aspects of the illustrative embodiments are implemented.
Figure 3:
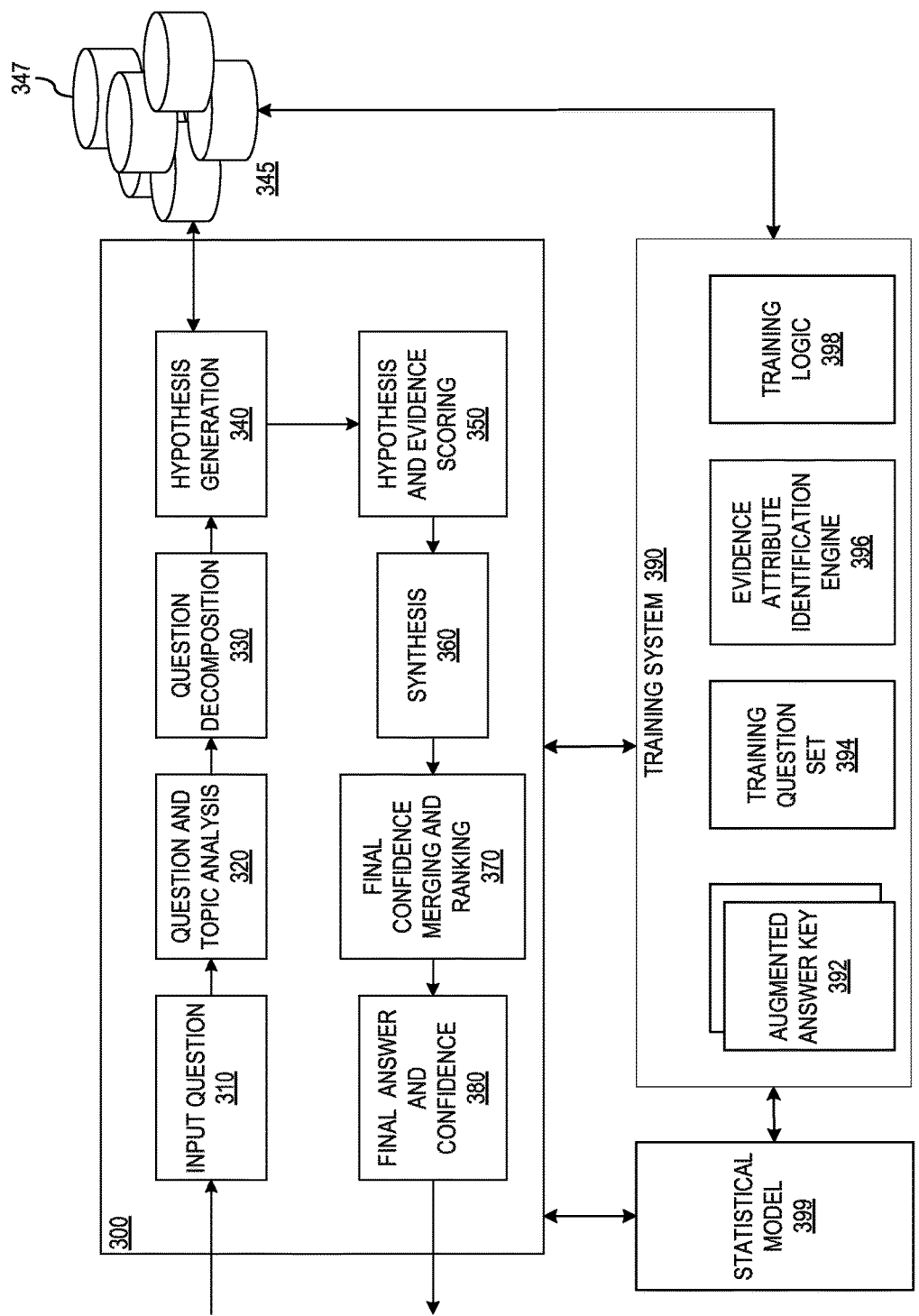
FIG. 3 illustrates a QA system pipeline for processing an input question in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example Question Answering (QA) system (also referred to as a Question/Answer system or Question and Answer system), methodology, and computer program product with which the mechanisms of the illustrative embodiments are implemented. As will be discussed in greater detail hereafter, the illustrative embodiments are integrated in, augment, and extend the functionality of these QA mechanisms with regard to training the QA system by augmenting the answer key with a spectrum or correct answers for the same training question and corresponding correlation attributes. The QA mechanisms are further augmented to select an entry in the answer key providing a correct answer from the spectrum based on the correspondence of attributes from the supporting evidence of a final answer generated by the QA system and then comparing the final answer with the entry in the answer key that was selected to thereby perform training of the QA system.

Thus, it is important to first have an understanding of how question and answer creation in a QA system is implemented before describing how the mechanisms of the illustrative embodiments are integrated in and augment such QA systems. It should be appreciated that the QA mechanisms described in FIGS. 1-3 are only examples and are not intended to state or imply any limitation with regard to the type of QA mechanisms with which the illustrative embodiments are implemented. Many modifications to the example QA system shown in FIGS. 1-3 may be implemented in various embodiments of the present invention without departing from the spirit and scope of the present invention.

As an overview, a Question Answering system (QA system) is an artificial intelligence application executing on data processing hardware that answers questions pertaining to a given subject-matter domain presented in natural language. The QA system receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA system. The document may include any file, text, article, or source of data for use in the QA system. For example, a QA system accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to the QA system which then answers the input questions using the content in the corpus of data by evaluating documents, sections of documents, portions of data in the corpus, or the like. When a process evaluates a given section of a document for semantic content, the process can use a variety of conventions to query such document from the QA system, e.g., sending the query to the QA system as a well-formed question which are then interpreted by the QA system and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA system receives an input question, parses the question to extract the major features of the question, uses the extracted features to formulate queries, and then applies those queries to the corpus of data. Based on the application of the queries to the corpus of data, the QA system generates a set of hypotheses, or candidate answers to the input question, by looking across the corpus of data for portions of the corpus of data that have some potential for containing a valuable response to the input question. The QA system then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA system. The statistical model is used to summarize a level of confidence that the QA system has regarding the evidence that the potential response, i.e. candidate answer, is inferred by the question. This process is repeated for each of the candidate answers until the QA system identifies candidate answers that surface as being significantly stronger than others and thus, generates a final answer, or ranked set of answers, for the input question.

As mentioned above, QA systems and mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA system to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA system. Content creators, automated tools, or the like, annotate or otherwise generate metadata for providing information useable by the QA system to identify these question and answer attributes of the content.

Operating on such content, the QA system generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a question/answer creation (QA) system 100 in a computer network 102. One example of a question/answer generation which may be used in conjunction with the principles described herein is described in U.S. patent application Publication No. 2011/0125734, which is herein incorporated by reference in its entirety. The QA system 100 is implemented on one or more computing devices 104 (comprising one or more processors and one or more memories, and potentially any other computing device elements generally known in the art including buses, storage devices, communication interfaces, and the like) connected to the computer network 102. The network 102 includes multiple computing devices 104 in communication with each other and with other devices or components via one or more wired and/or wireless data communication links, where each communication link comprises one or more of wires, routers, switches, transmitters, receivers, or the like. The QA system 100 and network 102 enables question/answer (QA) generation functionality for one or more QA system users via their respective computing devices 110-112. Other embodiments of the QA system 100 may be used with components, systems, sub-systems, and/or devices other than those that are depicted herein.

The QA system 100 is configured to implement a QA system pipeline 108 that receive inputs from various sources. For example, the QA system 100 receives input from the network 102, a corpus of electronic documents 106, QA system users, and/or other data and other possible sources of input. In one embodiment, some or all of the inputs to the QA system 100 are routed through the network 102. The various computing devices 104 on the network 102 include access points for content creators and QA system users. Some of the computing devices 104 include devices for a database storing the corpus of data 106 (which is shown as a separate entity in FIG. 1 for illustrative purposes only). Portions of the corpus of data 106 may also be provided on one or more other network attached storage devices, in one or more databases, or other computing devices not explicitly shown in FIG. 1. The network 102 includes local network connections and remote connections in various embodiments, such that the QA system 100 may operate in environments of any size, including local and global, e.g., the Internet.

In one embodiment, the content creator creates content in a document of the corpus of data 106 for use as part of a corpus of data with the QA system 100. The document includes any file, text, article, or source of data for use in the QA system 100. QA system users access the QA system 100 via a network connection or an Internet connection to the network 102, and input questions to the QA system 100 that are answered by the content in the corpus of data 106. In one embodiment, the questions are formed using natural language. The QA system 100 parses and interprets the question, and provides a response to the QA system user, e.g., QA system user 110, containing one or more answers to the question. In some embodiments, the QA system 100 provides a response to users in a ranked list of candidate answers while in other illustrative embodiments, the QA system 100 provides a single final answer or a combination of a final answer and ranked listing of other candidate answers.

The QA system 100 implements a QA system pipeline 108 which comprises a plurality of stages for processing an input question and the corpus of data 106. The QA system pipeline 108 generates answers for the input question based on the processing of the input question and the corpus of data 106. The QA system pipeline 108 will be described in greater detail hereafter with regard to FIG. 3.

In some illustrative embodiments, the QA system 100 may be the IBM Watson™ QA system available from International Business Machines Corporation of Armonk, N.Y., which is augmented with the mechanisms of the illustrative embodiments described hereafter. As outlined previously, the IBM Watson™ QA system receives an input question which it then parses to extract the major features of the question, that in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question. The IBM Watson™ QA system then performs deep analysis on the language of the input question and the language used in each of the portions of the corpus of data found during the application of the queries using a variety of reasoning algorithms. The scores obtained from the various reasoning algorithms are then weighted against a statistical model that summarizes a level of confidence that the IBM Watson™ QA system has regarding the evidence that the potential response, i.e. candidate answer, is inferred by the question. This process is be repeated for each of the candidate answers to generate ranked listing of candidate answers which may then be presented to the user that submitted the input question, or from which a final answer is selected and presented to the user. More information about the IBM Watson™ QA system may be obtained, for example, from the IBM Corporation website, IBM Redbooks, and the like. For example, information about the IBM Watson™ QA system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As shown in FIG. 1, the QA system 100 is augmented to include the training system 120 which includes an augmented answer key data structure 130 and corresponding training logic 140 configured to evaluate the correlation attributes of the augmented answer key data structure 130 with attributes of supporting evidence for final answers generated by the QA system 100. The augmented answer key data structure 130 is augmented such that a spectrum of correct answers for the same training question are defined as entries in the augmented answer key data structure 130. Differentiation between the various entries for the same training question is performed based on a matching of attributes of the supporting evidence for the final answer to correlation attributes specified in the entries of the answer key. An entry in the answer key is selected based on a matching of the attributes of the supporting evidence with the correlation attributes and the answer associated with the selected entry is then used to evaluate the correctness of the final answer generated by the QA system 100. In some illustrative embodiments, the correlation attributes may further specify personal preferences of the subject of the question or request. In such embodiments, the personal preferences of the subject may be provided as input with the question or request or may be otherwise identified through analysis of a data structure associated with the subject, or through analysis of the corpus or corpora used by the QA system 100.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a QA system 100 and QA system pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 8®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 illustrates a QA system pipeline for processing an input question in accordance with one illustrative embodiment. The QA system pipeline of FIG. 3 may be implemented, for example, as QA system pipeline 108 of QA system 100 in FIG. 1. It should be appreciated that the stages of the QA system pipeline shown in FIG. 3 are implemented as one or more software engines, components, or the like, which are configured with logic for implementing the functionality attributed to the particular stage. Each stage is implemented using one or more of such software engines, components or the like. The software engines, components, etc. are executed on one or more processors of one or more data processing systems or devices and utilize or operate on data stored in one or more data storage devices, memories, or the like, on one or more of the data processing systems. The QA system pipeline of FIG. 3 is augmented, for example, in one or more of the stages to implement the improved mechanism of the illustrative embodiments described hereafter, additional stages may be provided to implement the improved mechanism, or separate logic from the pipeline 300 may be provided for interfacing with the pipeline 300 and implementing the improved functionality and operations of the illustrative embodiments.

As shown in FIG. 3, the QA system pipeline 300 comprises a plurality of stages 310-380 through which the QA system operates to analyze an input question and generate a final response. In an initial question input stage 310, the QA system receives an input question that is presented in a natural language format. That is, a user inputs, via a user interface, an input question for which the user wishes to obtain an answer, e.g., "Who are Washington's closest advisors?" In response to receiving the input question, the next stage of the QA system pipeline 300, i.e. the question and topic analysis stage 320, parses the input question using natural language processing (NLP) techniques to extract major features from the input question, and classify the major features according to types, e.g., names, dates, or any of a plethora of other defined topics. For example, in the example question above, the term "who" may be associated with a topic for "persons" indicating that the identity of a person is being sought, "Washington" may be identified as a proper name of a person with which the question is associated, "closest" may be identified as a word indicative of proximity or relationship, and "advisors" may be indicative of a noun or other language topic.

In addition, the extracted major features include key words and phrases classified into question characteristics, such as the focus of the question, the lexical answer type (LAT) of the question, and the like. As referred to herein, a lexical answer type (LAT) is a word in, or a word inferred from, the input question that indicates the type of the answer, independent of assigning semantics to that word. For example, in the question "What maneuver was invented in the 1500s to speed up the game and involves two pieces of the same color?," the LAT is the string "maneuver." The focus of a question is the part of the question that, if replaced by the answer, makes the question a standalone statement. For example, in the question "What drug has been shown to relieve the symptoms of ADD with relatively few side effects?," the focus is " drug" since if this word were replaced with the answer, e.g., the answer "Adderall" can be used to replace the term "drug" to generate the sentence "Adderall has been shown to relieve the symptoms of ADD with relatively few side effects." The focus often, but not always, contains the LAT. On the other hand, in many cases it is not possible to infer a meaningful LAT from the focus.

Referring again to FIG. 3, the identified major features are then used during the question decomposition stage 330 to decompose the question into one or more queries that are applied to the corpora of data/information 345 in order to generate one or more hypotheses. The queries are generated in any known or later developed query language, such as the Structure Query Language (SQL), or the like. The queries are applied to one or more databases storing information about the electronic texts, documents, articles, websites, and the like, that make up the corpora of data/information 345. That is, these various sources themselves, different collections of sources, and the like, represent a different corpus 347 within the corpora 345. There may be different corpora 347 defined for different collections of documents based on various criteria depending upon the particular implementation. For example, different corpora may be established for different topics, subject matter categories, sources of information, or the like. As one example, a first corpus may be associated with healthcare documents while a second corpus may be associated with financial documents. Alternatively, one corpus may be documents published by the U.S. Department of Energy while another corpus may be IBM Redbooks documents. Any collection of content having some similar attribute may be considered to be a corpus 347 within the corpora 345.

The queries are applied to one or more databases storing information about the electronic texts, documents, articles, websites, and the like, that make up the corpus of data/information, e.g., the corpus of data 106 in FIG. 1. The queries are applied to the corpus of data/information at the hypothesis generation stage 340 to generate results identifying potential hypotheses for answering the input question, which can then be evaluated. That is, the application of the queries results in the extraction of portions of the corpus of data/information matching the criteria of the particular query. These portions of the corpus are then analyzed and used, during the hypothesis generation stage 340, to generate hypotheses for answering the input question. These hypotheses are also referred to herein as "candidate answers" for the input question. For any input question, at this stage 340, there may be hundreds of hypotheses or candidate answers generated that may need to be evaluated.

The QA system pipeline 300, in stage 350, then performs a deep analysis and comparison of the language of the input question and the language of each hypothesis or "candidate answer," as well as performs evidence scoring to evaluate the likelihood that the particular hypothesis is a correct answer for the input question. As mentioned above, this involves using a plurality of reasoning algorithms, each performing a separate type of analysis of the language of the input question and/or content of the corpus that provides evidence in support of, or not in support of, the hypothesis. Each reasoning algorithm generates a score based on the analysis it performs which indicates a measure of relevance of the individual portions of the corpus of data/information extracted by application of the queries as well as a measure of the correctness of the corresponding hypothesis, i.e. a measure of confidence in the hypothesis. There are various ways of generating such scores depending upon the particular analysis being performed. In generally, however, these algorithms look for particular terms, phrases, or patterns of text that are indicative of terms, phrases, or patterns of interest and determine a degree of matching with higher degrees of matching being given relatively higher scores than lower degrees of matching.

Thus, for example, an algorithm may be configured to look for the exact term from an input question or synonyms to that term in the input question, e.g., the exact term or synonyms for the term "movie," and generate a score based on a frequency of use of these exact terms or synonyms. In such a case, exact matches will be given the highest scores, while synonyms may be given lower scores based on a relative ranking of the synonyms as may be specified by a subject matter expert (person with knowledge of the particular domain and terminology used) or automatically determined from frequency of use of the synonym in the corpus corresponding to the domain. Thus, for example, an exact match of the term "movie" in content of the corpus (also referred to as evidence, or evidence passages) is given a highest score. A synonym of movie, such as "motion picture" may be given a lower score but still higher than a synonym of the type "film" or "moving picture show." Instances of the exact matches and synonyms for each evidence passage may be compiled and used in a quantitative function to generate a score for the degree of matching of the evidence passage to the input question.

Thus, for example, a hypothesis or candidate answer to the input question of "What was the first movie?" is "The Horse in Motion." If the evidence passage contains the statements "The first motion picture ever made was 'The Horse in Motion' in 1878 by Eadweard Muybridge. It was a movie of a horse running," and the algorithm is looking for exact matches or synonyms to the focus of the input question, i.e. "movie," then an exact match of "movie" is found in the second sentence of the evidence passage and a highly scored synonym to "movie," i.e. "motion picture," is found in the first sentence of the evidence passage. This may be combined with further analysis of the evidence passage to identify that the text of the candidate answer is present in the evidence passage as well, i.e. "The Horse in Motion." These factors may be combined to give this evidence passage a relatively high score as supporting evidence for the candidate answer "The Horse in Motion" being a correct answer.

It should be appreciated that this is just one simple example of how scoring can be performed. Many other algorithms of various complexity may be used to generate scores for candidate answers and evidence without departing from the spirit and scope of the present invention.

In the synthesis stage 360, the large number of scores generated by the various reasoning algorithms are synthesized into confidence scores or confidence measures for the various hypotheses. This process involves applying weights to the various scores, where the weights have been determined through training of the statistical model employed by the QA system and/or dynamically updated. For example, the weights for scores generated by algorithms that identify exactly matching terms and synonym may be set relatively higher than other algorithms that are evaluating publication dates for evidence passages. The weights themselves may be specified by subject matter experts or learned through machine learning processes that evaluate the significance of characteristics evidence passages and their relative importance to overall candidate answer generation.

The weighted scores are processed in accordance with a statistical model generated through training of the QA system that identifies a manner by which these scores may be combined to generate a confidence score or measure for the individual hypotheses or candidate answers. This confidence score or measure summarizes the level of confidence that the QA system has about the evidence that the candidate answer is inferred by the input question, i.e. that the candidate answer is the correct answer for the input question.

The resulting confidence scores or measures are processed by a final confidence merging and ranking stage 370 which compares the confidence scores and measures to each other, compares them against predetermined thresholds, or performs any other analysis on the confidence scores to determine which hypotheses/candidate answers are the most likely to be the correct answer to the input question. The hypotheses/candidate answers are ranked according to these comparisons to generate a ranked listing of hypotheses/candidate answers (hereafter simply referred to as "candidate answers"). From the ranked listing of candidate answers, at stage 380, a final answer and confidence score, or final set of candidate answers and confidence scores, are generated and output to the submitter of the original input question via a graphical user interface or other mechanism for outputting information.

The QA system pipeline 300 uses annotators to perform analysis of the corpus and evaluate the corpus with regard to the generation of candidate answers and corresponding scores based on supporting evidence in the corpus or corpora. Annotators represent logic that analyzes and scores various aspects of the content of the corpus 347 or corpora 345 to thereby identify candidate answers, supporting evidence, and generate confidence scores associated with the candidate answers based on the supporting evidence. Different annotators may be provided for analyzing the content of the corpus 347 or corpora 345 with regard to different criteria, e.g., one annotator may identify synonyms while another annotator may evaluate the focus of the question or request against a portion of content in the corpus. The annotators evaluate the portions of content in the corpus to determine matching of the portion of content with features of the question or request.

As shown in FIG. 3, a training system 390 is also provided in association with the QA system pipeline 300 and operates to train a statistical model 399 used to modify the weights applied to the results generated by annotators of the QA system pipeline 300 so as to improve the operation of the QA system pipeline 300 and increase the likelihood that correct answers are returned by the QA system pipeline 300 for input questions or requests. The model 399 is a statistical model reflecting how various answer scoring algorithms, i.e. annotators, employed within the QA system pipeline 300 should be weighted to yield optimal results/accuracy based on the set of training cases (training question and corresponding correct answer) used for training The statistical model 399 is used by the QA system pipeline 300 during training and at runtime to evaluate cases (training or new cases) presented to the QA system pipeline. During training, the model 399 is not actually "trained" as of yet, but is continuously modified as needed depending upon the results generated by the QA system pipeline 300 in response to the submission of training cases. Once the training system 390 determines that the QA system pipeline 300 is outputting candidate answers and corresponding confidence scores that are within an acceptable tolerance of the correct answers and confidence scores specified by the augmented answer key 392, the training may be discontinued and the then existing trained model 399 may be used as the final trained model 399 for the QA system pipeline 300 to be used during runtime operation.

During runtime, the trained model 399 has been trained using the training cases and augmented answer key 392 and represents the then determined optimal weights to be applied to the annotators (or scoring algorithms) of the QA system pipeline 300. Candidate answers for new cases are evaluated by first running the QA system pipeline 300 answer scoring algorithms (annotators) and then applying the weighting factors from the machine learning-derived trained model 399 to yield an overall confidence level for each candidate answer. This may be done, for example, during the hypothesis and evidence scoring stage 350 in FIG. 3, for example.

In accordance with the mechanisms of the illustrative embodiments, for one or more of the training questions in the training question set 394 used by the training system 390 to train the QA system pipeline 300, a spectrum of correct answers are generated and stored in association with the training question in entries in the augmented answer key 392, such as a question/answer pair. The entries further include associated correlation attributes that correlate the particular entry with a particular set of evidential attributes. Thus, entries in the augmented answer key 392 comprise question/answer pairs and associated correlation attributes with multiple entries being associated with the same training question in the training question set 394.

As one example, for the training question Q1 (or request) for a treatment recommendation for a cancer patient, multiple augmented answer key entries may be provided as follows:

Entry 1: Q1/high bone marrow blast (A1); age=<70, high white blood cell count, personal preference does not include "not hair loss" and "not nausea;"

Entry 2: Q1/Ara-c (high intensity)(A2); age=<120, high white blood cell count, personal preference includes "not hair loss" or "not nausea." Thus, in this example, multiple entries are associated with question Q1 and provide different answers A1-A2 of a spectrum of answers for the question Q1 that are determined to be correct for various conditions represented by the correlation attributes. The correlation attributes specify the conditions under which the corresponding answer A1 or A2 is the correct answer for the training question. It should be noted that the correlation attributes may, but do not require, attributes specifying conditions precedent in the supporting evidence of a final answer generated by the QA system pipeline 300 and attributes corresponding to personal preferences of the subject of the question or request, e.g., in this case the patient for which the treatment recommendation is requested.

Thus, the illustrative embodiments provide a mechanism to define a spectrum of acceptable answers and the circumstances or conditions in which they apply. This spectrum is defined in the answer key used to train the QA system by supplementing entries in the QA system with key correlation attributes used to differentiate circumstances and conditions in which one answer should be preferred over another, or considered "more correct" than another answer. The particular answer of an entry is considered to be the correct answer when corresponding attributes of the supporting evidence for a final answer are found to align with corresponding attributes of the entry in the answer key.

The answer key entry augmented with correlation attributes can also serve as a template for multiple training cases, i.e. training question and corresponding correct answer. That is, the spectrum of correct answers for all training cases which align on the specified set of correlation attributes may be designated and used to train the QA system. These separate sets of correlation attributes may be established as separate answer keys 392 where each answer key 392 corresponds to a particular set of correlation attributes and the correct answer key 392 is selected based on the determined attributes from the supporting evidence of the final answer generated by the QA system.

In addition, as noted above, based on the subject's own preferences, the best answer may not be the optimal answer and instead another answer may be more correct for the particular individual based on their preferences. The personal preferences are accommodated in the augmented answer key 392 by include key correlation attributes that reflect the particular personal preferences of the subject of the request or question, e.g., "not hair loss" and "not nausea" in the above example. These personal preferences may be used to train the QA system to reflect optimal recommendations when personal preferences are taken into account. Such personal preferences of a particular user may be supplied as input to the QA system pipeline 300 with the request/question 310 or otherwise identified through analysis of the corpus, e.g., patient medical history documents, or other such data structure. For example, in the medical domain, a patient's medical record may include designations of patient preferences including whether the patient is willing to endure nausea or hair loss during treatment (as may be solicited from the patient by a manual or electronic questionnaire or other method and added to appropriate fields of the patient medical record).

In operation, during a training mode of operation for the QA system pipeline 300, a training question from the training question set 394 is input to the QA system pipeline 300 as input question 310. In some illustrative embodiments, in addition, one or more preferences of the subject of the training question are also input to the QA system pipeline 300 for use in selecting a correct entry in the augmented answer key data structure 392 for the particular subject's preferences. The input question is processed through the QA system pipeline 300 in the manner previously described above to generate a final answer to the input question. In the process, the results of the annotators are captured and used for further analysis to generate the model 399. Moreover, the supporting evidence passages from the corpus 347 or corpora 345 that support the final answer as being the correct answer for the input question 310 are submitted to the training system 390 along with any preferences input with the question 310.

The evidence attribute identification engine 396 analyzes the supporting evidence passages for the final answer and extracts attributes from the supporting evidence passages, e.g., age of the patient, white blood cell count of the patient, personal preferences of the patient, etc. The extracted attributes and any preferences input with the question 310 are used by the training logic 398, along with an identifier of the training question, to search the augmented answer key data structure 392 to identify a matching entry for the training question that correlates with the evidence attributes. Thus, there may be 10 entries in the augmented answer key 392 for the input training question 310 and these entries are searched based on the identified evidence attributes to select an entry that has corresponding correlation attributes that most match the evidence attributes. By "most match", what is meant is that in some cases there may not be a perfect match of correlation attributes to evidence attributes but an entry having the most correlation attributes matched by the evidence attributes may be selected for use in evaluating the correctness of the final answer.

The answer of the entry selected from the augmented answer key 392 is compared by the training logic 398 to the final answer generated by the QA system pipeline 300 for the input question 310. Based on whether or not the answers match, the training logic 398 modifies the model 399 to adjust weights to be applied to annotators to modify their scoring of features of evidence for generation of candidate answers and corresponding confidence scores. This adjustment of weights may be performed using any generally known machine learning approach, supervised learning, or any other suitable learning operation which is modified to operate using the augmented answer key mechanisms of the illustrative embodiments. Examples of learning processes that may be used to adjust weights in general are described in various Wikipedia pages including those associated with the terms "training set," "machine learning," and "supervised learning". This process may be repeated until an amount of change in the model 399 is less than a predetermined threshold in which case it is determined that the model 399 is accurate enough to cause the QA system pipeline 300 to generate correct answers at an acceptable level of accuracy. The QA system pipeline 300 is then determined to have been trained and can then be used during runtime processing of non-training questions.

Figure 4:
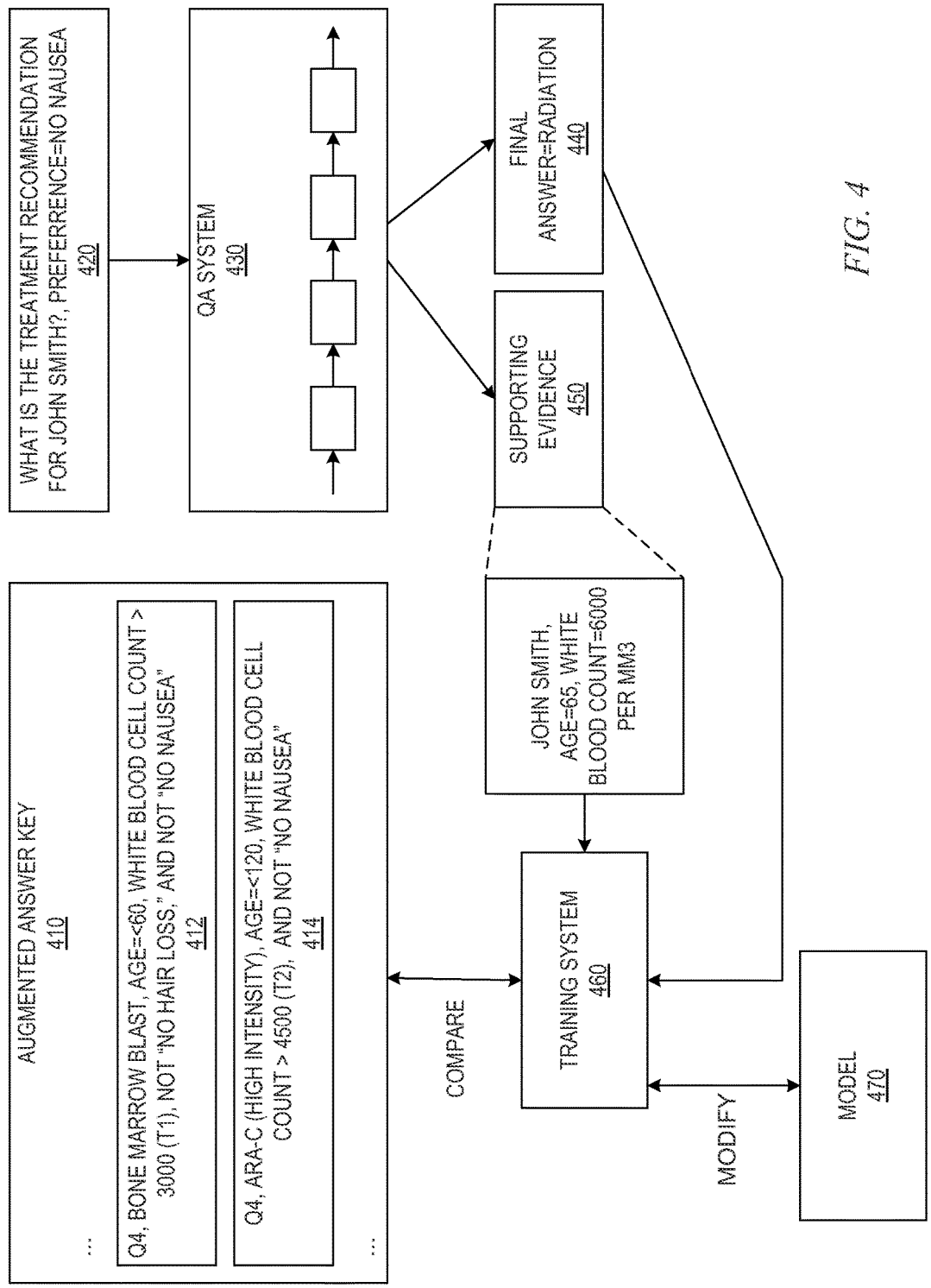
FIG. 4 is an example block diagram illustrating an operation for evaluating an answer generated by a QA system pipeline using an augmented answer key in accordance with one illustrative embodiment.

To illustrate the operation of the illustrative embodiments more clearly, consider the example shown in FIG. 4. FIG. 4 is an example block diagram illustrating an operation for evaluating an answer generated by a QA system pipeline using an augmented answer key in accordance with one illustrative embodiment. As shown in FIG. 4, an augmented answer key 410 is provided that includes, among other answer key entries, a set of answer key entries 412-414 for the training question 420 "what is the treatment recommendation for John Smith?" Each answer key entry has an identifier of the question that it corresponds to, the correct answer, and one or more correlation attributes identifying the conditions under which the entry provides the most correct answer. Thus, for example, the augmented answer key entry 412 comprises the question identifier Q4 corresponding to the above question, a corresponding answer of "bone marrow blast," and correlation attributes of age=<60 white blood cell count above threshold T1, not "no hair loss", and not "no nausea." Similarly, augmented answer key entry 414 comprises the question identifier Q4 corresponding to the above question, a corresponding answer of "Ara-C (high intensity)", and correlation attributes of age=<120, white blood cell count above threshold T2, and not "no nausea."

The input question 420, and possibly one or more subject preferences, e.g., "no nausea", are input to the QA system 430 which processes the input question 420 and generates a final answer 440 and corresponding supporting evidence 450. The supporting evidence 450 is provided to the training system 460 which extracts attributes from the supporting evidence 450 and searches the augmented answer key 410 for the entries 412 and 414 corresponding to the input question 420. The correlation attributes of the entries 412 and 414 are compared to the evidence attributes extracted from the supporting evidence 450. In the depicted example, the supporting evidence 450 includes a patient medical record for the patient John Smith which includes information about John Smith's age, i.e. 65, and his white blood count, i.e. 6000 per mm3. These attributes may be compared against the correlation attributes of the entries 412 and 414. Since John Smith is not equal to or less than 60 years old, entry 412 does not provide the best answer under the circumstances. However, with regard to entry 414, John Smith is equal to or less than 120 years of age (basically anyone is a candidate for this entry), and his white blood count is above the threshold T2 of 4500 per mm3, i.e. is a normal white blood count. Thus, it appears that entry 414 provides the most correct answer for the particular conditions as identified from the supporting evidence.

Now, suppose that with the input question 420, a personal preference of John Smith is input that indicates that John Smith does not want to experience nausea as part of the treatment. In such a case, the personal preference causes the entry 414 to not be fully matched, i.e. entry 414 specifies that there not be a "no nausea" preference, yet in this scenario the patient clearly requests "no nausea." However, as noted above, the mechanisms of the illustrative embodiments do not require a full match of all attributes. Thus, even though entry 414 is not fully matched, it has the most matches of the applicable entries in the augmented answer key 410 and thus, is selected as the entry 414 for evaluating the operation of the QA system 430 and training the model 470.

Having selected entry 414 as representing the most correct answer for the conditions, the answer specified in entry 414 is compared to the final answer 440. If the two match, then no adjustment of the model 470 is necessary. If there are discrepancies between the answer specified in the entry 414 and the final answer 440, then weights associated with annotators of the QA system 430 are modified to improve the operation of the QA system 430. Thus, for example, in the depicted scenario, the answer in the entry 414 is Ara-C, yet the final answer 440 generated by the QA system 430 is radiation treatments. Because of the discrepancy, the logic of the training system 460 determines which annotators were most influential in generating the final answer 440 and their weights are adjusted to reduce their influence while other annotators may have their weights increased to increase their relative contribution to the scoring of candidate answers. This process may be repeated in an iterative manner using the same and/or different training questions in a training question set to perform additional training of the model 470 until a degree of change in the model 470 is less than a predetermined threshold at which time the model 470 is determined to have been trained and ready to use during runtime operation.

Figure 5:
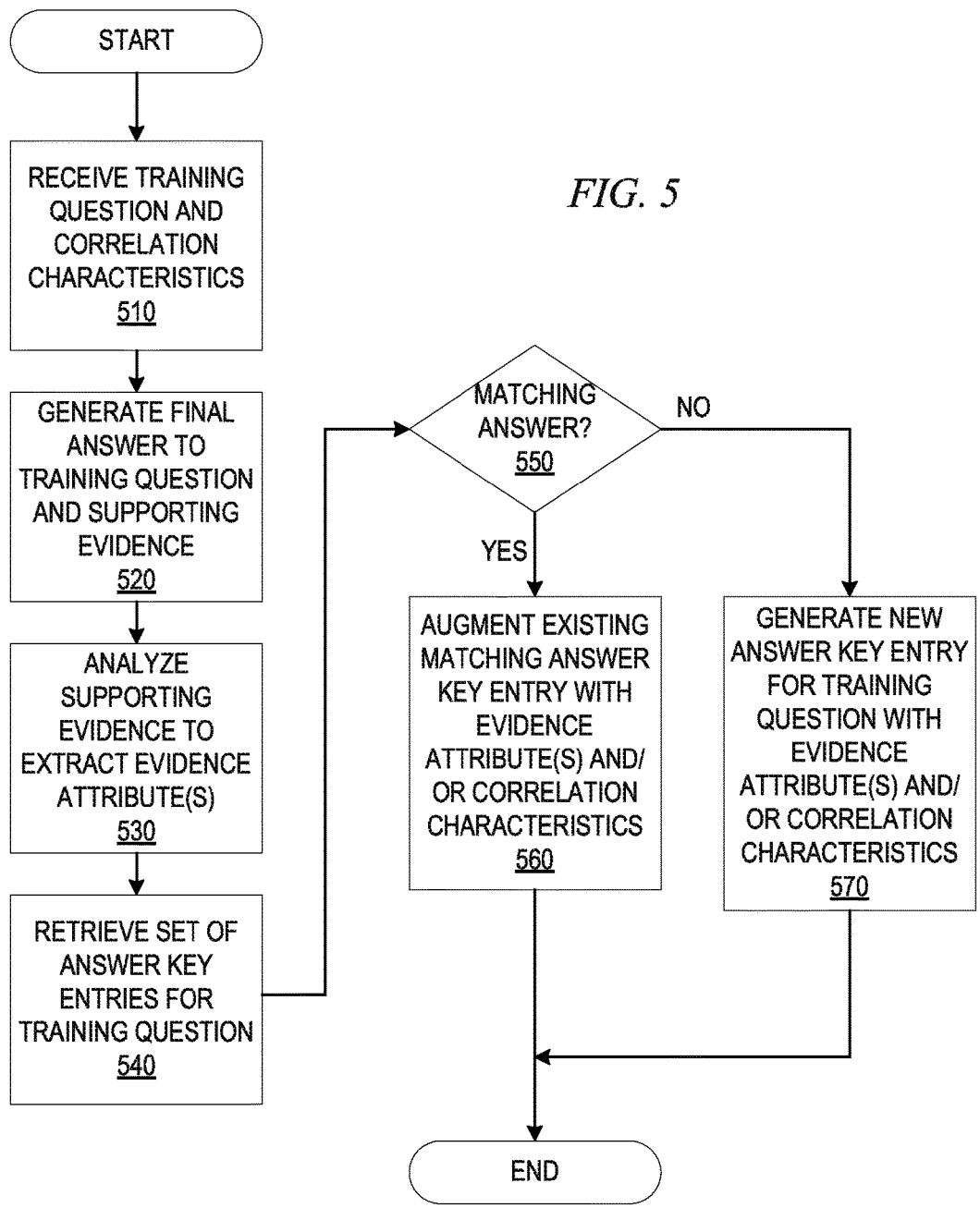
FIG. 5 is a flowchart outlining an example operation for generating an augmented answer key in accordance with one illustrative embodiment.

FIG. 5 is a flowchart outlining an example operation for generating an augmented answer key in accordance with one illustrative embodiment. As shown in FIG. 5, the operation start with receiving a training question, and associated correlation characteristics, for which one or more answers exist in association with the training question in an answer key data structure (step 510). The training question is processed to generate a final answer to the training question and corresponding supporting evidence for the final answer based on a corpus of information and the correlation characteristics (step 520). The supporting evidence is analyzed to identify one or more evidence attributes (step 530). One or more correct answer entries in the answer key data structure, associated with the training question, are identified (step 540) and a determination is made as to whether a correct answer in the answer key data structure is present that matches the final answer generated through processing the training question (step 550).

If there is a matching correct answer, evidence attributes in the supporting evidence and/or correlation characteristics associated with the training question are added to an answer key entry corresponding to the correct answer in the answer key to thereby generate an augmented answer key (step 560). In this way, the answer key entry corresponding to the matching correct answer is more heavily weighted during future processing of questions when correlation characteristics or evidence attributes associated with the question substantially match the evidence attributes associated with the correct answer in the augmented answer key data structure.

If there is no matching correct answer in the answer key, the answer key is updated to include an additional answer key entry corresponding to the training question which includes the final answer and the evidence attributes and/or correlation characteristics associated with the final answer (step 570). The operation then terminates. While FIG. 5 shows the operation terminating, this process may be repeated for additional training questions and/or additional combinations of training questions and correlation characteristics, e.g., the same training question may be submitted with different correlation characteristics so as to generate additional augmented answer keys and/or augmented answer key entries associated with the training question.

Figure 6:
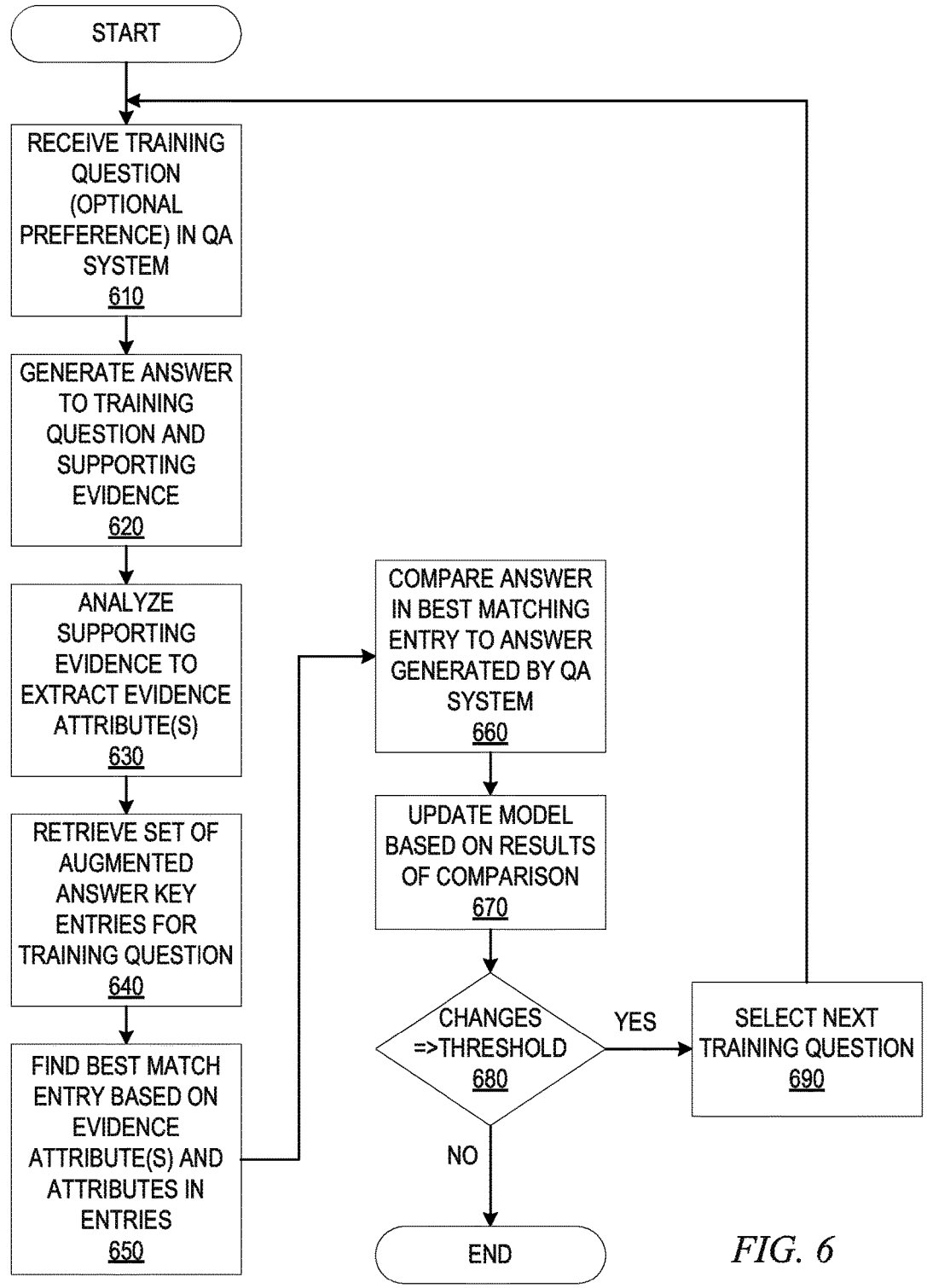
FIG. 6 is a flowchart outlining an example operation for training a QA system in accordance with one illustrative embodiment.

FIG. 6 is a flowchart outlining an example operation for training a QA system in accordance with one illustrative embodiment. As shown in FIG. 6, the operation starts with a training question and optional subject preferences being input to the QA system (step 610). The question is processed by the QA system to generate a final answer to the question and supporting evidence for the final answer (step 620). The supporting evidence is analyzed to extract one or more evidence attributes (step 630). A set of entries corresponding to the training question is identified in an augmented answer key (step 640) and a search of the set of entries is performed based on the evidence attributes to find a best matching entry having one or more matching correlation attributes in the entries (step 650). The answer associated with the best matching entry is then compared to the final answer generated by the QA system (step 660) and a model of weight values is updated based on results of the comparison (step 670).

A determination is made as to whether changes to the model were equal to or greater than a predetermined threshold (step 680). If so, then a next training question is selected (step 690) and input to the QA system thereby returning to step 610. If the changes are less than the predetermined threshold, then the training is complete and the operation terminates.

Thus, the illustrative embodiments provide mechanisms for providing a spectrum of correct answers for training questions and specifying the conditions under which one correct answer is determined to be "more correct" than other correct answers. Thus, training may be performed taking into account the variability of correct answers. Moreover, training may further be performed based on personal preferences of the subject to the question/request.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory and implementing training logic for training a Question and Answer (QA) system of the data processing system, the method comprising:

configuring the data processing system to cause the data processing system to execute the training logic for training the QA system based on an augmented answer key data structure;

receiving, by the QA system, a training question;

processing, by the QA system, the training question to generate a final answer to the training question and supporting evidence for the final answer based on an electronically stored corpus of information;

analyzing, by the training logic executing in the data processing system, the supporting evidence to identify one or more evidence attributes;

searching, by the training logic, a plurality of correct answer entries in an answer key associated with the training question, to identify a matching correct answer entry in the answer key that matches the final answer, wherein the answer key is a data structure storing known correct answers to correlated training questions in a training question set data structure;

augmenting, by the training logic, the matching correct answer entry in the answer key to include the one or more evidence attributes, to thereby generate the augmented answer key data structure; and training, by the training logic, the QA system, based on the augmented answer key data structure, to generate a trained QA system.

2. The method of claim 1, wherein the one or more evidence attributes are one or more evidence attributes that differentiate conditions of supporting evidence under which a corresponding correct answer entry is more correct for the training question than other correct answer entries for the training question.

3. The method of claim 1, wherein the augmented answer key data structure defines, for each training question, a spectrum of correct answers and corresponding circumstances under which each correct answer in the spectrum of correct answers is determined to be more correct than other correct answers in the spectrum of correct answers.

4. The method of claim 1, wherein the training question is a question for recommending a medical treatment for a patient, the one or more evidence attributes comprises characteristics of the patient, and wherein the final answer is a medical treatment recommendation.

5. The method of claim 1, wherein the one or more evidence attributes comprises one or more personal preferences of an individual represented in information in the corpus of information.

6. The method of claim 1, wherein the augmented answer key data structure is one of a plurality of augmented answer key data structures, and wherein each augmented answer key data structure is associated with a different set of evidence attributes from other augmented answer key data structures in the plurality of augmented answer key data structures.

7. The method of claim 6, further comprising:
receiving, by the QA system, one or more correlation characteristics associated with the training question, wherein training the QA system comprises selecting an augmented answer key data structure from the plurality of augmented answer key data structures based on the one or more correlation characteristics submitted with the training question, and training the QA system using one or more correct answer entries for the training question stored in the selected augmented answer key data structure.

8. The method of claim 1, wherein training the QA system comprises:
receiving, by the QA system, the training question;
processing, by the QA system, the training question to generate a candidate answer to the training question and supporting evidence for the candidate answer based on a search of the corpus of information;
selecting, by the QA system, a set of correct answers for the training question from the augmented answer key data structure;
comparing, by the QA system, the candidate answer and supporting evidence for the candidate answer to the set of correct answers and evidence attributes associated with each correct answer in the set of correct answers; and
modifying an operation of the QA system based on results of the comparison.

9. The method of claim 8, wherein modifying the operation of the QA system comprises modifying weights associated with annotators of the QA system in a statistical model associated with the QA system.

10. The method of claim 1, further comprising:
answering, by the trained QA system, a subsequent question submitted to the trained QA system.

11. A computer program product comprising a computer readable storage medium having a computer readable program stored therein, wherein the computer readable program, when executed on a data processing system implementing a Question and Answer (QA) system and associated training logic, causes the data processing system to:
configure the data processing system to execute the training logic for training the QA system based on an augmented answer key data structure;
receive, by the QA system, a training question;
process, by the QA system, the training question to generate a final answer to the training question and supporting evidence for the final answer based on an electronically stored corpus of information;
analyze, by the training logic executing in the data processing system, the supporting evidence to identify one or more evidence attributes;
search, by the training logic, a plurality of correct answer entries in an answer key associated with the training question, to identify a matching correct answer entry in the answer key that matches the final answer, wherein the answer key is a data structure storing known correct answers to correlated training questions in a training question set data structure;
augment, by the training logic, the matching correct answer entry in the answer key to include the one or more evidence attributes, to thereby generate the augmented answer key data structure; and
train, by the training logic, the QA system based on the augmented answer key data structure to generate a trained QA system.

12. The computer program product of claim 11, wherein the one or more evidence attributes are one or more evidence attributes that differentiate conditions of supporting evidence under which a corresponding correct answer entry is more correct for the training question than other correct answer entries for the training question.

13. The computer program product of claim 11, wherein the augmented answer key data structure defines, for each training question, a spectrum of correct answers and corresponding circumstances under which each correct answer in the spectrum of correct answers is determined to be more correct than other correct answers in the spectrum of correct answers.

14. The computer program product of claim 11, wherein the training question is a question for recommending a medical treatment for a patient, the one or more evidence attributes comprises characteristics of the patient, and wherein the final answer is a medical treatment recommendation.

15. The computer program product of claim 11, wherein the one or more evidence attributes comprises one or more personal preferences of an individual represented in information in the corpus of information.

16. The computer program product of claim 11, wherein the augmented answer key data structure is one of a plurality of augmented answer key data structures, and wherein each augmented answer key data structure is associated with a different set of evidence attributes from other augmented answer key data structures in the plurality of augmented answer key data structures.

17. The computer program product of claim 16, wherein the computer readable program further causes the data processing system to receive, by the QA system, one or more correlation characteristics associated with the training question, wherein the computer readable program further causes the data processing system to train the QA system at least by selecting an augmented answer key data structure from the plurality of augmented answer key data structures based on the one or more correlation characteristics submitted with the training question, and training the QA system using one or more correct answer entries for the training question stored in the selected augmented answer key data structure.

18. The computer program product of claim 11, wherein the computer readable program further causes the data processing system to train the QA system at least by:
receiving, by the QA system, the training question;

processing, by the QA system, the training question to generate a candidate answer to the training question and supporting evidence for the candidate answer based on a search of the corpus of information;

selecting, by the QA system, a set of correct answers for the training question from the augmented answer key data structure;

comparing, by the QA system, the candidate answer and supporting evidence for the candidate answer to the set of correct answers and evidence attributes associated with each correct answer in the set of correct answers; and modifying an operation of the QA system based on results of the comparison.

19. The computer program product of claim 18, wherein the computer readable program further causes the data processing system to modify the operation of the QA system at least by modifying weights associated with annotators of the QA system in a statistical model associated with the QA system.

20. An apparatus comprising:
a processor; and
a memory coupled to the processor, wherein the memory comprises instructions which, when executed by the processor, cause the processor to:

configure the processor to execute training logic for training a Question and Answer (QA) system based on an augmented answer key data structure;

receive a training question;

process the training question to generate a final answer to the training question and supporting evidence for the final answer based on an electronically stored corpus of information;

analyze, by the training logic executing on the processor, the supporting evidence to identify one or more evidence attributes;

search a plurality of correct answer entries in an answer key associated with the training question, to identify a matching correct answer entry in the answer key that matches the final answer, wherein the answer key is a data structure storing known correct answers to correlated training questions in a training question set data structure;

augment, by the training logic, the matching correct answer entry in the answer key to include the one or more evidence attributes, to thereby generate the augmented answer key data structure; and train, by the training logic, the OA system based on the augmented answer key data structure to generate a trained QA system.

* * * * *